United States Patent
Lapierre-Landry et al.

(10) Patent No.: US 10,682,053 B2
(45) Date of Patent: Jun. 16, 2020

(54) OPHTHALMIC PHOTOTHERMAL OPTICAL COHERENCE TOMOGRAPHY APPARATUS

(71) Applicant: Wisconsin Alumni Research Foundation, Madison, WI (US)

(72) Inventors: Maryse Lapierre-Landry, Madison, WI (US); Melissa Skala, Middleton, WI (US); Yuankai Tao, Nashville, TN (US)

(73) Assignees: Wisonsin Alumni Research Foundation, Madison, WI (US); Vanderbilt University, Nashville, TN (US)

(*) Notice: Subject to any disclaimer, the term of this patent is extended or adjusted under 35 U.S.C. 154(b) by 103 days.

(21) Appl. No.: 15/940,108

(22) Filed: Mar. 29, 2018

(65) Prior Publication Data
US 2019/0298167 A1    Oct. 3, 2019

(51) Int. Cl.
*A61B 3/10* (2006.01)
*G01B 9/02* (2006.01)
*A61B 3/12* (2006.01)
*A61B 3/14* (2006.01)

(52) U.S. Cl.
CPC ........... *A61B 3/102* (2013.01); *A61B 3/12* (2013.01); *A61B 3/1225* (2013.01); *A61B 3/14* (2013.01); *G01B 9/02091* (2013.01)

(58) Field of Classification Search
CPC ......... A61B 3/102; A61B 3/12; A61B 3/1225; A61B 3/14; G01B 9/02091
See application file for complete search history.

(56) References Cited

PUBLICATIONS

Lapierre Landry et al. "In vivo photothermal optical coherence tomography of endogenous and exogenous contrast agents in the eye." Scientific reports 7, No. 1; pp. 1-9 (Aug. 2017): 9228. US.
Hrebesh M. Subhash et al. "Optical detection of indocyanine green encapsulated biocompatible poly (lactic-co-glycolic) acid nanoparticles with photothermal optical coherence tomography." Optics letters 37, No. 5 (2012): pp. 981-983. US.
Jason M. Tucker-Schwartz et al. "Photothermal optical lock-in optical coherence tomography for in vivo imaging." Biomedical optics express 6, No. 6 (2015): pp. 2268-2282. US.

*Primary Examiner* — Jack Dinh
(74) *Attorney, Agent, or Firm* — Boyle Fredrickson S.C.

(57) ABSTRACT

An optical coherence tomography system for ophthalmic use identifies tissue by selected laser heating of that tissue at reduced power levels decreasing background noise to boost signal-to-noise ratio allowing detection of minute changes in thermal expansion caused by that heating at clinically acceptable levels.

19 Claims, 4 Drawing Sheets

OPHTHALMIC PHOTOTHERMAL OPTICAL COHERENCE TOMOGRAPHY APPARATUS

STATEMENT REGARDING FEDERALLY SPONSORED RESEARCH OR DEVELOPMENT

Not applicable

CROSS REFERENCE TO RELATED APPLICATION

Not applicable

BACKGROUND OF THE INVENTION

The present invention relates generally to diagnostic imaging equipment for the human eye and in particular to an optical coherence tomography machine using thermal stimulation.

Optical coherence tomography (OCT) is widely used to study retinal diseases, for example, including macular degeneration (AMD), diabetic retinopathy, and glaucoma. In OCT studies of the eye, light is projected into retinal tissue where it reflects off of boundaries between tissue layers in the retina having different indices of refraction. The length of time required for the reflected light to return can be used to produce a depth-image of tissue layers analogous to that obtained in ultrasonic imaging.

The high speeds of light propagation (compared, for example, to propagation speed of ultrasound) is accommodated by deducing light transit time indirectly by looking at interference between the outgoing light and returning light using an interferometer and subsequent processing.

Ideally, the different tissue layers in the retina could be "highlighted" by using a tissue-selective contrast material preferentially retained by the tissue of one layer and introduced into the retina or by using pigments naturally present in certain retinal layers. Unfortunately, conventional contrast materials suitable for use in the eye do not significantly alter the index of refraction of the tissue and are thus are largely ineffective in emphasizing particular tissue in OCT imaging, the latter of which relies on phase differences generated by reflections at boundaries between tissues having different indices of refraction rather than on absorption of the tissue or contrast material.

SUMMARY OF THE INVENTION

The present invention provides for the application of photothermal heating to particular tissue layers to emphasize those layers when using OCT. In this technique, the pigment, while not directly visible in OCT, selectively absorbs light from a "thermal" laser that heats the tissue. This heating produces localized thermal expansion causing slight shifts in the dimension of the layers that can be detected in OCT. This detection process compares the location of the layers in the heated and unheated images and provides a faint signal that allows the pigmented layer to be uniquely identified by its expansion.

The use of photothermal heating with OCT is generally known for non-retinal tissue using laser powers and pigment concentrations that are unacceptable for the human eye. Prior to the present invention, it was reasonably expected that reducing the power level and/or pigment concentration to levels suitable for clinical observation of the human eye would predictably cause the faint photothermal signal to be disappeared into known background mechanical and thermal fluctuations of living tissue including mechanical vibration, electrical noise, as well as thermal and mechanical fluctuations caused by breathing and heartbeat of the subject.

Contrary to expectations, the present inventors have discovered that the background signal is strongly dependent on the energy of the thermal laser (apparently being in significant part a thermal phenomenon and a thermal phenomenon caused by the laser). For this reason, significant reduction of thermal laser power to clinically acceptable levels unexpectedly reduces background noise sufficiently to permit photothermal OCT to be employed as a clinically-appropriate eye imaging technique.

Specifically, then, the present invention provides an ophthalmic retina evaluation system including an OCT light source and a photothermal light source providing modulated photothermal light at a predetermined frequency. A lens system then focuses combined light from the optical modulator and the OCT light source through a lens of a human eye in vivo onto a human retina to return a reflected signal. An optical system divides the reflected signal into reflection components each associated with a depth in the retina. An electronic computer receives values of the reflection components and executes a stored program to: (1) analyze the changes in the apparent depths of the reflection components as a function of modulation of the photothermal light to identify heating of the tissue as a function of apparent depth range; and (2) output information isolating retinal tissue at a depth range having a predetermined threshold of heating. The light from the photothermal light source measured at an output of the lens system incident to a position of the eye has an average power of less than 1 mw over a 0.7 mm diameter aperture.

It is thus a feature of at least one embodiment of the invention to permit photothermal optical coherence tomography in clinical application to the human retina.

The light from the OCT light source and photothermal light source as modulated when measured at an output of the lens system incident to a position of the eye may have an average power of less than 1 mw over a 0.7 mm diameter aperture.

It is thus a feature of at least one embodiment of the invention to reduce the power level of the light sources sufficiently so that the combination of light power remains at an appropriate level.

The photothermal light source may project the light on the retina for a duration of less than 100 ms during a 5 second interval.

It is thus a feature of at least one embodiment of the invention to limit the total duration of light exposure at a location of the retina to increase the permissible maximum power.

The optical modulator may operate at a frequency greater than 100 hertz with an on-duty cycle of less than 60 percent.

It is thus a feature of at least one embodiment of the invention to move the thermal signal away from the frequency of natural biological processes while accommodating maximum heating and cooling difference.

The output information may provide a depth image of the retina including the isolated retinal tissue at a depth range within the retina.

It is thus a feature of at least one embodiment of the invention to permit accurate depth measurements of retinal layers.

Alternatively, or in addition, the output information may provide a quantitative volumetric measurement of isolated retinal tissue within a predetermined area.

It is thus a feature of at least one embodiment of the invention to permit an isolation of layers such as allows quantitative measurement of retinal layer volume that may be useful for the detection and monitoring of degenerative diseases.

The ophthalmic retina evaluation system may include a camera providing an image of the retina and the computer may store at least one retina template image having a marked region to correlate the retina template image with the image of the retina to locate the predetermined region.

It is thus a feature of at least one embodiment of the invention to permit accurate longitudinal studies of changes in retinal tissue volume by allowing reproducible assessment of particular retinal areas.

The output may be a chart showing change in volume of the isolated retinal tissue over time.

It is thus a feature of at least one embodiment of the invention to provide an intuitive output indicating retinal changes.

The photothermal light source may provide light centered on a peak frequency of absorption of indocyanine green (ICG) or fluorescein.

It is thus a feature of at least one embodiment of the invention to provide a system that can work with clinically acceptable contrast agents.

The photothermal light may provide light centered on a peak frequency of absorption of melanin.

It is thus a feature of at least one embodiment of the invention to provide a system that can work with naturally occurring pigments in the retinal tissue eliminating the need for contrast agents.

These particular objects and advantages may apply to only some embodiments falling within the claims and thus do not define the scope of the invention.

DETAILED DESCRIPTION OF THE PREFERRED EMBODIMENT

Figure 1:
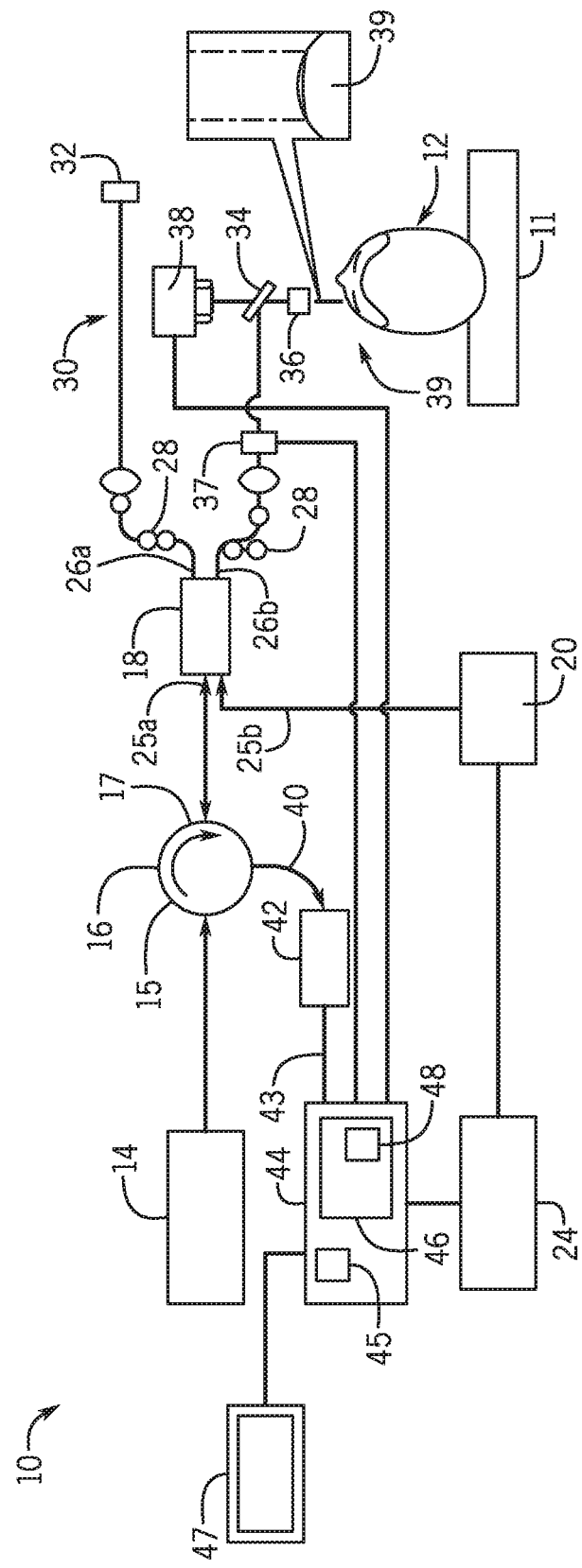
FIG. 1 is a block diagram of the optical circuit of the tomography apparatus of the present invention showing an imaging and a thermal light source.

Referring now to FIG. 1, the present invention provides an ophthalmic retina evaluation system 10 suitable for measurement of retinal tissue of human patients 12.

The retina evaluation system 10 includes a first OCT light source 14 providing a broadband light signal, in one example, centered about 860 nanometers with the 93-nanometer bandwidth. This OCT light source 14 may employ a super luminescent diode of a type commercially available from Inphenix, Inc., CA, USA.

Light from the OCT light source 14 is conducted by an optical fiber to a first port 15 of an optical circulator 16 providing a direction sensitive beam splitting as will be discussed below. A suitable optical circulator 16 is commercially available from AC Photonics, Inc. of Santa Clara, Calif., USA.

Light from a downstream port 17 of the optical circulator is then received by a first fiber input port 25a of a 50:50 fiber optic coupler 18. The fiber optic coupler 18 operates to combine light from the OCT light source 14 received at the fiber input port 25a with light from a thermal light source 20 as will be discussed below received at fiber input port 25b. The combined light is then divided between two fiber output ports 26a and 26b. Generally, the terms "input" and "output" are for descriptive convenience, it being understood that the fiber optic coupler 18 working bidirectionally.

The thermal light source 20 providing light received at the second input port 25b of the fiber optic coupler 18 may be provided by laser diode having a wavelength of 685 nanometers, for example, of a type commercially available from Coherent, Inc. of Santa Clara Calif., USA. Light from the thermal light source 20 is modulated by a waveform generator 24, for example, of type commercially available from SciCore Instruments, NJ, USA. The function generator 24 is controlled to chop (by turning the laser diode on and off) the light beam from the thermal light source 20 at a 50 percent duty cycle at 500 hertz. A signal from the waveform generator 24 may also be provided to the computer 44 to assist in demodulating the thermal signal as will be discussed below.

Alternatively, it will be appreciated that the thermal light source 20 may be modulated by other devices including for example and acoustical optic modulator or the like. L.

Combined light from the OCT light source 14 and the thermal light source 20 from the fiber optic coupler 18 exit through each of the output ports 26a and 26b to be received by a corresponding polarization controller 28. A light beam from port 26a after passing through polarization controller 28 travels along a reference path 30 to a mirror 32 to return and be received at the output port 26a.

At the same time, light from output port 26b, after passing through polarization controller 28 is received by a galvanometer scanner 37 to allow scanning of the beam in a raster pattern over a predetermined region of interest of the eye 39 of the patient 26. This scanned light is received by beam splitter 34 and objective lens 36 for projection into the eye 39 through the front lens of the eye 39 to an image plane on the retina. The galvanometer scanner 37 allows positioning of the focal spot in an arbitrary location within the field of view on the retina.

Generally, the strength of the thermal light source 20 exiting the objective lens 36 and received by the eye 39 provides a controlled average power over a circular area having a diameter of seven millimeters corresponding to a fully dilated average human eye. This average power is limited to less than three milliwatts and typically less than one milliwatt and preferably to an average power of 0.3-2 milliwatts as measured at the location of the eye 39, for example, with the head of the patient 12 positioned on the positioner 11.

Light reflected back from the retina of the eye 39 travels backward through the lens 36 and the beam splitter 34 to be received again at port 26b.

Light received by ports 26*a* and 26*b* exits from the fiber optic coupler 18 in part at port 25*a* to pass backward to the optical circulator 16 which conducts this light to a third port 40 of the optical circulator 16 to be received by a spectrometer 42. The spectrometer 42 may include a charge-coupled camera (not shown) for providing a spectrographic signal 43 of the received light, for example, as separated by an optical grating or the like.

It will be appreciated that the necessary data may be alternatively acquired by sweeping the frequency of the OCT light source 14 and using a single photodetector whose output is linked to the particular frequency of the OCT light source 14 at a particular time. The system operates functionally as a spectrometer that does not require an optical grating or the like to separate light frequencies. Accordingly, the term "spectrometer" maybe held to embrace any device that can analyze separate light frequencies either in a broadband light source or a swept light source.

The spectrographic signal will show intensity variations at different frequencies of the OCT outputted light that relate to constructive and destructive interference between the light traveling on the path to the eye 39 versus the path to the mirror 32. This interference will be a function of the phase difference of these light portions which in turn is a function of the frequency of the light and the distance traveled by the light for reflection in the eye 39. As a result, analysis of the interference as a function of frequency indicates a depth of reflection within the eye 39.

This spectrographic signal 43 may be digitized and received by the computer having a processor 45 communicating with a memory 46 holding a stored program 48 for processing the spectrographic signal 43. Generally, this processing will convert the spectrum into a depth and intensity signal (using the Fourier transform) providing an indication of intensity of light received from different layers of the retina. The computer 44 may control the galvanometer scanner 37 to produce a series of A-scans (revealing light reflection at different depths at a single point on the retina), or B-scan images of the retina (revealing depth information along a line perpendicular to depth) as is generally understood in the art. These scans may be displayed on a graphic terminal 47 or the like communicating with the computer 44.

The retina evaluation system 10 may further include a standard digital camera 38 positioned near the beam splitter 34 to receive a portion of the light reflected back from the eye 39 provided either from the OCT light source 14 or a separate ring light positioned around the camera lens of the camera 38. In this way the camera 38 and the spectrometer 42 may simultaneously use the lens 36 to obtain a conventional microscope image of the retina and OCT information both of which will be provided to the computer 44 for processing as will be described.

The frequency of the thermal light source 20 will be set to an absorption peak of a pigment or contrast agent associated with a particular layer of structure in the retina that needs to be emphasized or measured. Acceptable pigments include melanin, and acceptable contrast agents include indocyanine green (ICG) having a peek absorption at about 685 nanometers and fluorescein having a peek absorption at about 494 nanometers.

Figure 2:
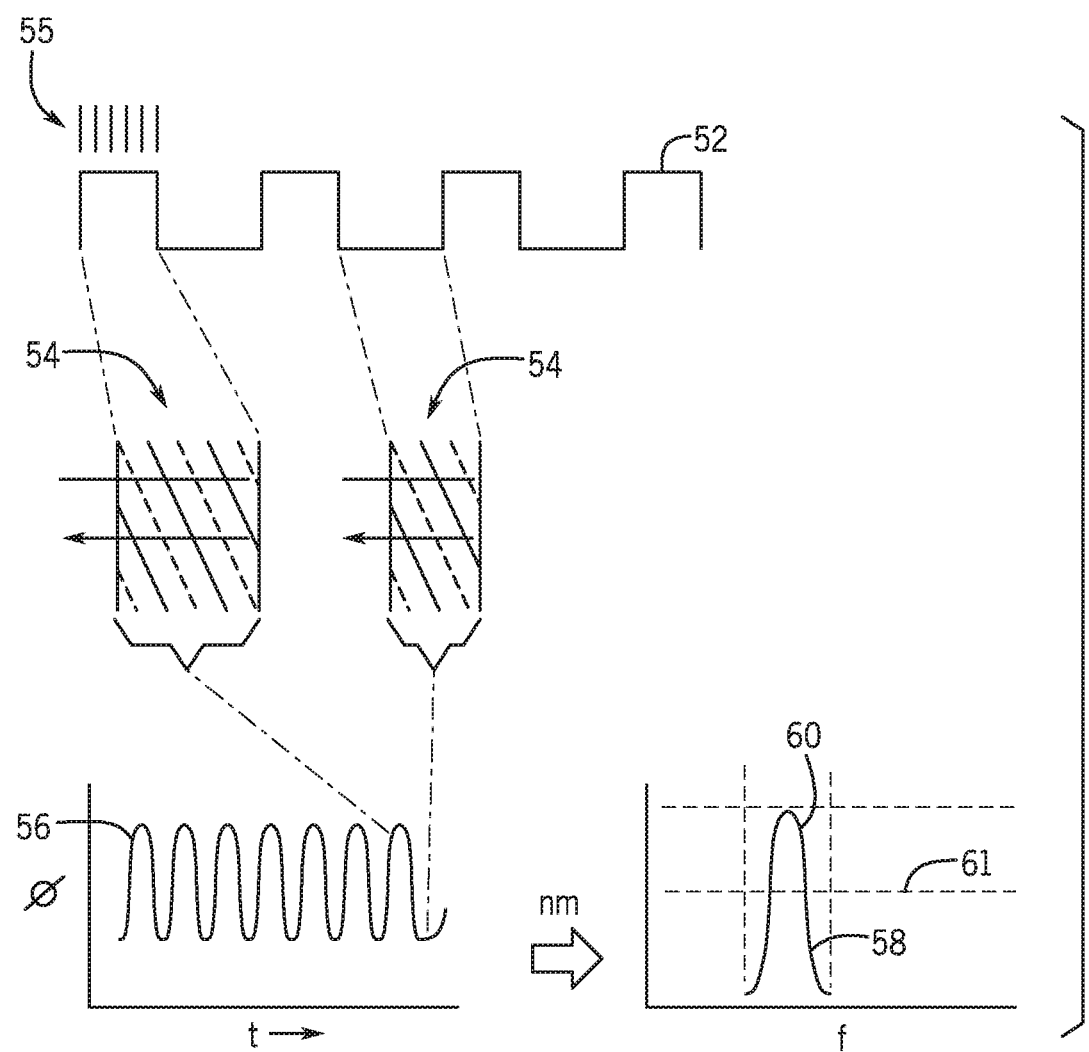
FIG. 2 is a set of signal diagrams showing the signals generated in the optical circuit of FIG. 1.

Referring now to FIG. 2, modulation of the thermal light source 50 may provide a square wave modulated light output 52 having a 50 percent duty cycle. During the on-time of the thermal light source 50, a tissue layer 54 having a contrast material or pigment of interest absorbs light from the thermal light source 50 and thermally expands producing a greater phase shift between the light reflected from the eye 39 versus the light reflected from the reference path and mirror 32. For example, during this time of thermal expansion, the light may constructively interfere to produce a peak of a phase signal 56 received from a given layer 54 (representing movement of the layer interfaces detected by the spectrometer 42 and processing by the computer 44). Conversely during times when the thermal light source 50 is off, thermal contraction may cause the heated layer 54 to shrink slightly reducing the phase shift of the signal 56 and producing a trough of the phase signal 56. The phase signal 56 represents a narrow range of frequencies of the light from the OCT light source 14 associated with layer 54.

This thermal expansion effect may be isolated by examining the apparent displacement of layers 54 in an OCT image and, for example, identifying a rate of change in the apparent position of the given layer between heating and cooling per modulated light output 52 to isolate the heated layer 54. More generally, a Fourier transform of the phase signal 56 within the narrowband around the modulation frequency of 500 hertz will provide a peak value 60 indicating the relative change in dimension of the layer 54 and will be termed the photothermal signal 58 for that frequency range. This peak 60 may be determined as exceeding a predetermined threshold 61 or a floating threshold based on a local maximum. The strength of the photothermal signal 58 controls the ability of the system to highlight the layer 54 containing the contrast medium or pigment in the presence of background noise related to normal temperature fluctuation and other artifacts associated with living tissue.

The present inventors have determined, as would be expected from theory, that the strength of the photothermal signal 58 varies approximately linearly with the power of the thermal light source 20. This alone suggests that reducing the power of the thermal light source 20 to clinical levels would cause the photothermal signal 58 to significantly degrade and disappear below the noise floor.

Figure 3:
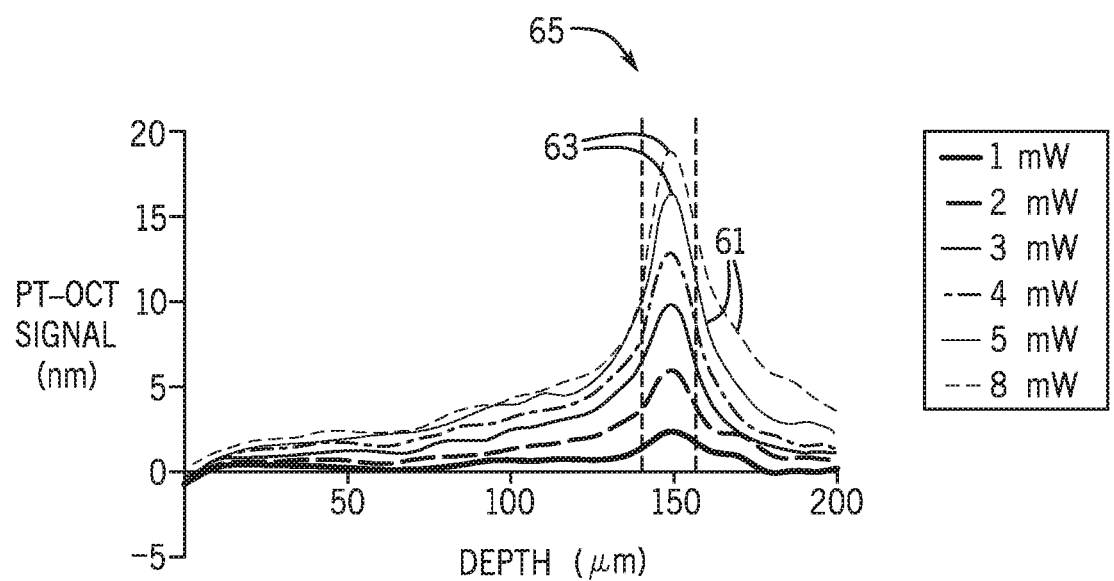
FIG. 3 is a chart showing the thermal signal as a function of depth for different laser powers windowed to show background levels.

Referring now to FIG. 3, a plot line 61 of peak values 60 of the photothermal signal 58 for different laser powers indicates the amount of apparent expansion of the tissue layer 54 in nanometers at those depth layers. As expected, the peak 63 of plot line 61 at the depth range of the layer 54 having the contrast medium or pigment drops as power decreases. Of note, however, is that the background noise level outside of the windows 64 also drops.

Figure 4:
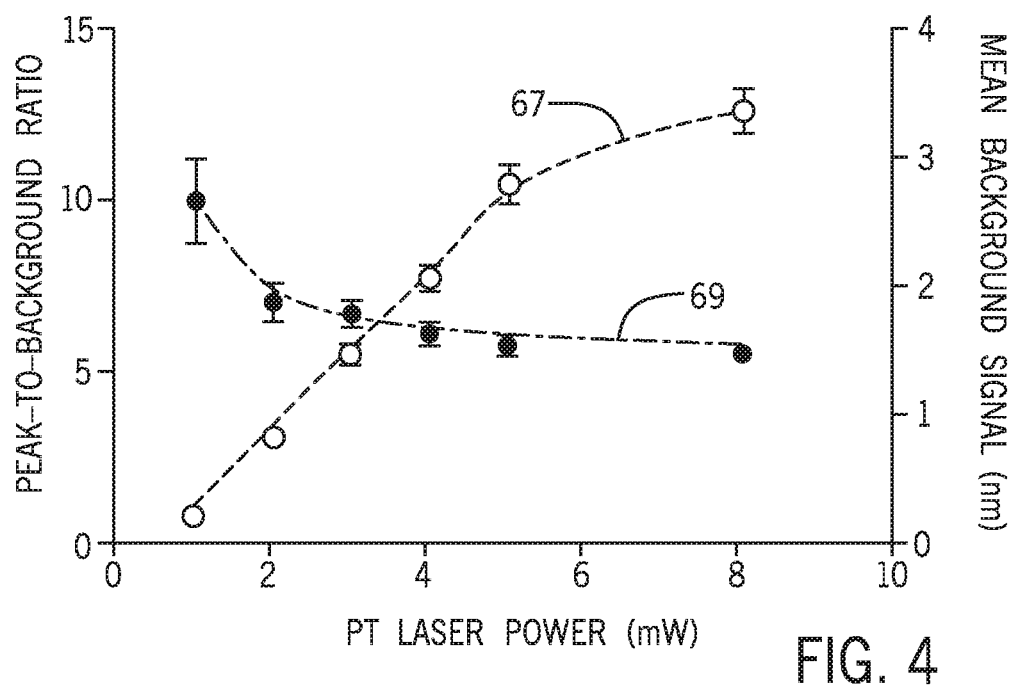
FIG. 4 is a chart showing signal-to-noise ratio of the thermal signal as a function of laser power and showing background signal as a function of laser power illustrating a strong dependency of the background signal on the laser power such as may operate to boost signal-to-noise ratio for low laser powers rendering PTOCT clinically acceptable for the human eye.

Referring now to FIG. 4, however, the present inventors have determined that although the signal peak 63 decreases with decreased power from the thermal light source 20 (per FIG. 3), the background noise 67 drops faster so that the signal-to-noise ratio 69 in fact rises with lower powers of the thermal light source 20. Although the inventors do not wish to be bound by a particular theory, this high dependency of background signal on thermal light source power is believed to result from an unexpectedly disproportional amount of heat propagating outward from the pigmented or contrast-infused layer 54 and/or increase in absorption of the pigmented or contrast-free layers above and below this layer 54. The result is a discovery that clinically acceptable low wattages of the thermal light source 20 may be expected to produce good quality OCT signals.

The present invention supplements this phenomenon with additional signal processing obtained by repeated and averaged measurements, for example, providing 700 repeated measurements of each sample point in the retina before moving to the next spot in the B-scan. Samples 55 (shown in FIG. 2) can be acquired at approximately 36 kilohertz. Details about signal processing techniques suitable for this purpose are described in Tucker-Schwartz, J. M., Meyer, T.

A., Patil, C. A., Duvall, C. L. & Skala, M. C.: In vivo photothermal optical coherence tomography of gold nanorods contrast agents. Biomedical Optics Express 3(11), 2882-2895 (2012) hereby incorporated by reference.

Figure 5:
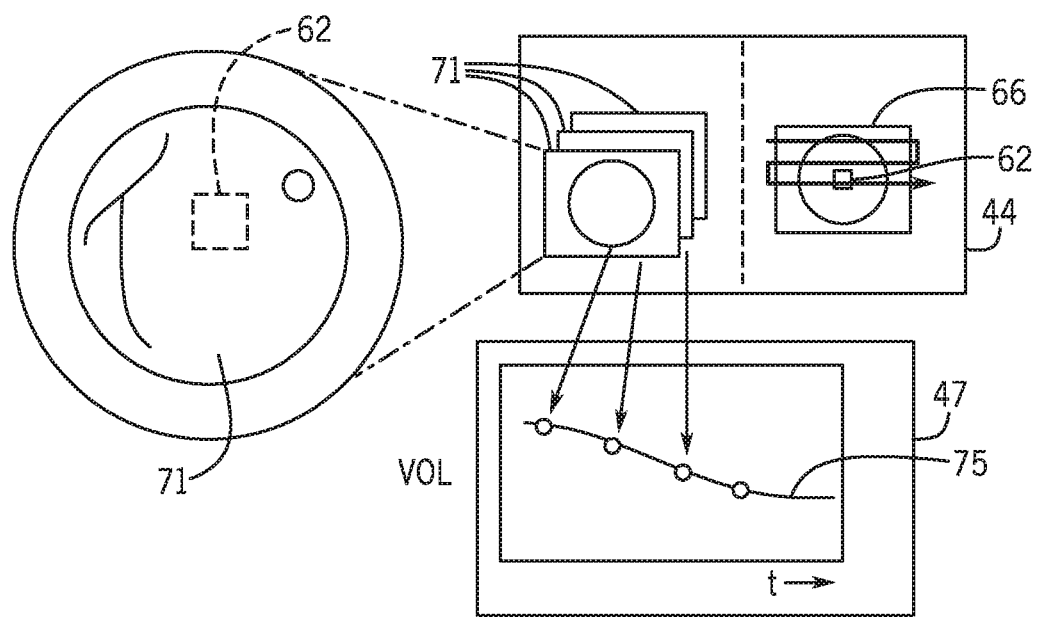
FIG. 5 is a diagram showing use of a template to a reproducibly located region of interest in the longitudinal retina evaluation.

Referring now to FIGS. 1 and 5, the present apparatus may be used to perform longitudinal studies of changes in retinal structures by providing quantitative volumetric measurements using a thickness dimension obtained by the PTOCT measurements over a registered areal region of interest 62. The region of interest 62 may be located in a sequence of time separated images 71 obtained by camera 38 and used to guide the galvanometer scanner 37. In this process, a first image 71 may be designated as reference image 66 and stored in memory 46 as a template associated with a particular patient 12 and having a defined region of interest 62 selected by the healthcare professional. At a later time, additional images 71 may be obtained and aligned by correlation with the template image 66 matching fiducial structure such as blood vessels and the like in the two images 71 and 66. With this correlation complete an identical region of interest 62' may be located in the later images 71 and the galvanometer scanner 37 controlled to acquire similar data in the same location. Data associated with each of the regions of interest 62 and 62' over time may be output by the computer on the graphic display screen 47 to show a progression plot 75, for example, indicating a change in volume of the retinal layer 54 over time to track the progress of diseases such as macular degeneration and possible effects of useful drugs in this regard.

Figure 6:
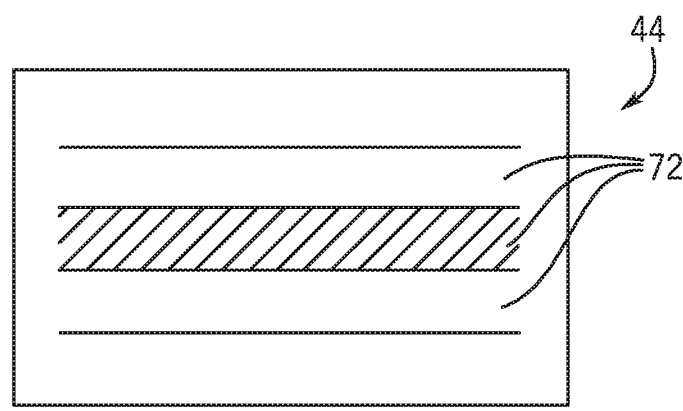
FIG. 6 is a figure of an output image highlighting a particular region using PTOCT.

Referring to FIG. 6, more generally the computer 44 may output on the graphic display screen 47 a cross-sectional B-scan image of the tissue of the retina showing various layers 72 and highlighting, for example, by color or the like a given layer 72' associated with the pigment or contrast as isolated using the photothermal signal described above. Alternatively, or in addition, the display screen 47 may show concentration of pigment or contrast agent which may also be indicated quantitatively. This concentration may be constrained to be that obtained within a predetermined volume (for example as identified above). In addition, the graphic display of concentration may be provided to the distributions can be determined. It is anticipated that melanin concentration may be a marker of disease and accordingly longitudinal changes in this concentration may have clinical significance.

This application hereby incorporates by reference: Maryse Lapierre-Landry et al: "In vivo photothermal optical coherence tomography of endogenous and exogenous contrast agents in the eye" Scientific Reports |7: 9228|Doi: 10.1038/S41598-017-10050-5 (Aug. 23, 2017).

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

As used herein "pigment" may refer equally to an artificial pigment introduced by way of a contrast medium or a naturally occurring pigment within tissue.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. An ophthalmic retina evaluation system comprising:
   an OCT light source;
   a photothermal light source providing modulated photothermal light at a predetermined frequency;
   a lens system operating to focus combined light from the OCT light source and photothermal light source through a lens of a human eye in vivo on a human retina and to return a reflected signal;
   an optical system dividing the reflected signal into reflection components each associated with a depth in the retina; and
   an electronic computer communicating with the optical system to receive values of the reflection components executing a stored program to:
   (1) analyze changes in apparent depths of the reflection components as a function of modulation of the modulated photothermal light to identify heating of retinal tissue of the human eye as a function of apparent depth range; and
   (2) output information isolating the retinal tissue at a depth range having a predetermined threshold heating;
   wherein the modulated photothermal light measured at an output of the lens system incident to a position of the human eye has an average power of less than 1 mw over a 0.7 mm diameter aperture.

2. The ophthalmic retina evaluation system of claim 1 wherein light from the OCT light source combined with the light from the modulated photothermal light source measured at an output of the lens system incident to a position of the human eye has an average power of less than 1 mw over a 0.7 mm diameter aperture.

3. The ophthalmic retina evaluation system of claim 1 wherein the photothermal light source projects the light on the retina for a duration of less than 100 ms during a 5 second interval.

4. The ophthalmic retina evaluation system of claim 1 wherein the modulated photothermal light has a frequency greater than 100 hertz with an on-duty cycle of less than 60 percent.

5. The ophthalmic retina evaluation system of claim 1 wherein the output information is a depth image of the retina including the isolated retinal tissue at a depth range within the retina.

6. The ophthalmic retina evaluation system of claim 1 wherein the output information is a quantitative volumetric measurement of isolated retinal tissue within a predetermined area.

7. The ophthalmic retina evaluation system of claim 6 further including a camera providing an image of the retina and wherein the electronic computer stores at least one retina template image having a marked region to correlate the retina template image with the image of the retina to locate the predetermined region.

8. The ophthalmic retina evaluation system of claim 1 wherein the output is a quantitative measurement of pigment concentration.

9. The ophthalmic retina evaluation system of claim 1 wherein the photothermal light source provides light centered on a peak frequency of absorption of indocyanine green (ICG).

10. The ophthalmic retina evaluation system of claim 1 wherein the photothermal light provides light centered on a peak frequency of absorption of fluorescein.

11. The ophthalmic retina evaluation system of claim 1 wherein the photothermal light provides light matching a frequency of absorption of melanin.

12. The ophthalmic retina evaluation system of claim 1 wherein the optical system is at least one of an interferometer and spectrometer.

13. A method of analyzing a human eye employing an ophthalmic retina evaluation system having:
   an OCT light source;
   a photothermal light source providing modulated photothermal light at a predetermined frequency;
   a lens system operating to focus combined light from the OCT light source and photothermal light source through a lens of a human eye in vivo on a human retina and to capture a reflected signal;
   an optical system dividing the reflected signal into reflection components each associated with a depth in the retina; and
   an electronic computer receiving values of the reflection components and executing a stored program to:
   (1) analyze changes in apparent depths of the reflection components as a function of modulation of the modulated photothermal light to identify heating of retinal tissue of a human eye as a function of apparent depth range; and
   (2) output information isolating the retinal tissue at a depth range having a predetermined threshold heating;
   the method comprising the steps of:
   (a) administering a contrast material to a patient for selective accumulation in a layer of the retina; and
   (b) employing the ophthalmic retina evaluation system to provide output information isolating the retinal tissue accumulating the contrast material;
   wherein the contrast material has a concentration of less than one milligram per milliliter as administered.

14. The method of claim 13 wherein the contrast material is selected from the group consisting of indocyanine green and fluorescein.

15. The method of claim 13 wherein the modulated photothermal light measured at an output of the lens system incident to a position of the human eye has an average power of less than 1 mw over a 0.7 mm diameter aperture.

16. The method of claim 13 wherein light from the OCT light source combined with light from the photothermal light source measured at an output of the lens system incident to a position of the human eye has an average power of less than 1 mw over a 0.7 mm diameter aperture.

17. The method of claim 13 wherein the photothermal light source projects the light on the retina for a duration of less than 100 ms during a 5 second interval.

18. The method of claim 13 wherein the modulated photothermal light has a frequency greater than 100 hertz with an on-duty cycle of less than 60 percent.

19. The ophthalmic retina evaluation system of claim 1 wherein the output is a chart showing change in at least one of volume of the isolated retinal tissue and concentration of pigment over time.

* * * * *